United States Patent
Kuriathungal et al.

(10) Patent No.: US 7,639,890 B2
(45) Date of Patent: Dec. 29, 2009

(54) AUTOMATIC SIGNIFICANT IMAGE GENERATION BASED ON IMAGE CHARACTERISTICS

(75) Inventors: Murali Kumaran Kuriathungal, Hoffman Estates, IL (US); Ashish Dolatrai Vassa, Palatine, IL (US)

(73) Assignee: General Electric Company, Schenectady, NY (US)

( * ) Notice: Subject to any disclaimer, the term of this patent is extended or adjusted under 35 U.S.C. 154(b) by 771 days.

(21) Appl. No.: 11/257,871

(22) Filed: Oct. 25, 2005

(65) Prior Publication Data

US 2007/0092142 A1  Apr. 26, 2007

(51) Int. Cl.
*G06K 9/40* (2006.01)
(52) U.S. Cl. ............... 382/260; 382/190; 382/209; 382/219
(58) Field of Classification Search ........ 382/181, 382/209, 219
See application file for complete search history.

(56) References Cited

U.S. PATENT DOCUMENTS

| | | | |
|---|---|---|---|
| 6,421,629 B1 * | 7/2002 | Ishiyama | 702/159 |
| 7,043,474 B2 * | 5/2006 | Mojsilovic et al. | 707/6 |
| 7,180,086 B2 * | 2/2007 | Leblans et al. | 250/584 |
| 7,272,593 B1 * | 9/2007 | Castelli et al. | 707/3 |
| 7,298,880 B2 * | 11/2007 | Nishiura | 382/128 |

OTHER PUBLICATIONS

Petricoin III, Emanuel; Ardekani, Ali M.; Hitt, Ben A.; Levin, Peter J.; Fusaro, Vincent A.; Steinberg, Seth M.; Mills, Gordon B.; Simone, Charles; Fishman, David A.; Kohn, Elise C.; Liotta, Lance A.; *Use of Proteomic Patterns in Serum to Identify Ovarian Cancer*, The Lancet, vol. 359:572-577, Feb. 16, 2002.

* cited by examiner

*Primary Examiner*—Yosef Kassa
(74) *Attorney, Agent, or Firm*—McAndrews, Held & Malloy, Ltd.; Peter J. Vogel; Michael A. Dellapenna

(57) ABSTRACT

The present invention provides for the automatic generation of a series of significant images. One or more representative significant images are used to generate a pattern description. The pattern description can include any information useful to identify an object of interest, or pattern. The pattern description can include a mathematical shape definition of one or more patterns, a search boundary defining an image area to search for matching patterns, and one or more pattern characteristics. The pattern description is compared to one or more images and one or more amounts of match between the pattern description and each image is obtained. The amount(s) of match are then compared to one or more thresholds. If one or more of the amounts of match exceed one or more thresholds or are within an upper and lower threshold window, then the image is automatically selected for inclusion in a series of significant images.

28 Claims, 9 Drawing Sheets

AUTOMATIC SIGNIFICANT IMAGE GENERATION BASED ON IMAGE CHARACTERISTICS

BACKGROUND OF THE INVENTION

The present invention generally relates to an improvement in the selection of significant images in a Picture Archiving and Communication Systems ("PACS"). Specifically, the present invention relates to the automatic generation of a set of significant images based on characteristics or patterns in images being examined.

PACS systems connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining healthcare operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

Once the image data has been preprocessed, a user (such as a radiologist) can access the image data from a display workstation. In general, a user may review several images in an imaging study (or a set of related images) in order to determine if any of the images are "significant." An image may be significant if one or more objects of interest appear in the image and/or these objects of interest appear in a particular location and/or orientation in the image. In other words, a radiologist may be examining a series of images in an imaging study that were obtained over a given time period. These images may be tracking the growth or development of a tumor in a patient anatomy, for example. The radiologist may wish to find all images that display the tumor in a given position, orientation, and/or size. Therefore, the radiologist can manually examine each image in the study to determine if any of the images are significant (that is, include the tumor in a given position, orientation, and/or size). If the radiologist determines that a given image is significant, the image may be electronically "marked" as significant.

An image may be significant if it is important for a diagnosis. For example, in diagnosing a tumor in an abdomen anatomy, of the many images acquired, only a few may indicate the presence of a tumor. These images may be marked as significant.

An image may be marked as significant by associating one or more attributes with data representative of the image. For example, an entry in a database corresponding to a significant image may be associated with one or more attributes that indicate the significance of the image.

A user may examine images with reference to a representative significant image. A representative significant image is an image that includes one or more objects of interest, or patterns, that the user is interested in. For example, a representative significant image may be a baseline image that all other images being examined are compared to. A radiologist may find an image in an imaging study that includes an object of interest or pattern in a given position, orientation and/or size, for example. The radiologist may then manually review all other images in the imaging study to determine if any of the other images include the same object of interest or pattern in the same position, orientation and/or size, for example. In this way, the radiologist manually reviews or examines images to determine if any of them include one or more patterns that match one or more patterns in the representative significant image.

With increasing volumes of examinations and images, a reduction of radiologists and mounting pressures on improved productivity, radiologists are in dire need of reducing the amount of their time spent manually reviewing and examining images for patterns that match one or more patterns in a representative significant image. For example, typical image data sets or imaging studies can include 3000 or more images which take up a considerable amount of time to read or review.

Therefore, a need exists for reducing the amount of time spent by users in reviewing images in one or more imaging studies to mark images as significant and therefore create sets of significant images. Such a need can be met by defining a pattern description that is based on one or more patterns in one or more representative significant images. This pattern description can include identified patterns in mathematical forms, pattern boundaries, and/or pattern characteristics. Using pattern matching or recognition, this pattern description can then be compared to one or more images in order to determine an amount of match between the pattern description and each image. If an amount of match exceeds or matches one or more thresholds, then the image may be automatically selected and marked as significant. This image may then be included in a set or subset of significant images.

Doing so would allow radiologists to more quickly identify images that are significant. Other than initially identifying the reference or representative significant image and the pattern description, no other manual intervention is required to generate a series of significant images. Moreover, as pattern descriptions may be saved for repeated use, users may more easily generate series of significant images from historical significant image pattern descriptions.

The present invention therefore allows for the generation of significant images from a pattern description generated from one or more historical images (that is, one or more representative significant images). This automated significant image generation allows radiologists to quickly generate one or more significant image series from historical and current imaging studies. By reducing the amount of time required for generating a significant image series, users may then spend more time reading and reviewing the significant images.

In addition, pattern descriptions of a prior imaging study can be used to generate significant images for a current imaging study. Such pattern descriptions may be based on a prior imaging study that has one or more of an imaged body part or anatomy, an imaging procedure, and a type of imaging modality in common with the current imaging study. Thus, it can be beneficial to add automatic generation of significant images for a current study based on the pattern descriptions of a previous comparison study.

BRIEF SUMMARY OF THE INVENTION

The present invention provides a method for automatic significant image generation based on image characteristics. The method includes comparing a pattern description to a plurality of images and based on the comparing step, selecting at least one significant image from the plurality of images. The pattern description includes one or more patterns based on a representative image.

The present invention also provides a method for generating a pattern description for automatically selecting one or more significant images. The method includes identifying one or more patterns in a representative significant image and characterizing the patterns in a pattern description by defining at least one of a shape, a search boundary, and an image characteristic of one or more of the objects of interest.

The present invention also provides a computer-readable storage medium including a set of instructions for a computer. The set of instructions include a pattern comparison routine and a significant image set generation routine. The pattern comparison routine is configured to compare a pattern description to a plurality of images. The pattern description includes one or more patterns in a representative image. The significant image set generation routine is configured to select at least one significant image from the plurality of images.

The present invention also provides a computer-readable storage medium including a set of instructions for a computer. The set of instructions include an input routine and a pattern description creation routine. The input routine is configured to identify one or more patterns in a representative significant image. The pattern description creation routine is configured to characterize the patterns in a pattern description by defining at least one of a shape, a search boundary, and an image characteristic of one or more of the patterns.

Figure 1:
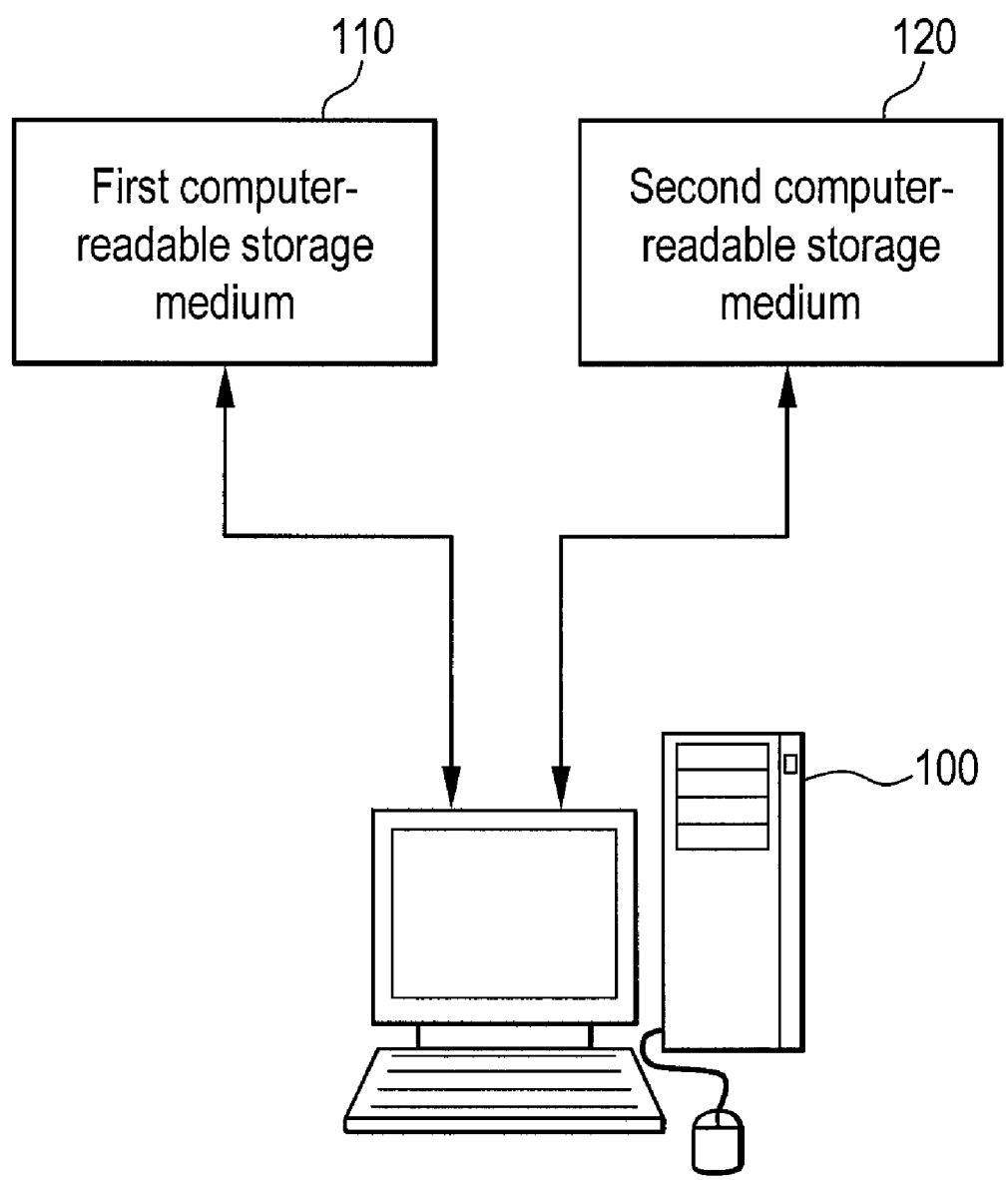
FIG. 1 illustrates a workstation and two computer readable storage media in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a workstation 100 and two computer readable storage media 110, 120 in accordance with an embodiment of the present invention. Any one or more of workstation 100 and media 110, 120 may be included in a PACS system. A PACS system can include any number of workstations 100 and/or computer-readable storage media 110, 120 and is not in any way limited to the embodiment of system 100 as illustrated in FIG. 1.

One or both of computer-readable storage media 110, 120 may be embodied in any type of memory known to those of ordinary skill in the art. In an embodiment, one or both of media 110, 120 may be included in a single physical storage media, such as a computer hard drive. In another embodiment, media 110, 120 are included in separate physical storage media, such as separate computer hard drives. In an embodiment, one or both of media 110, 120 may be included in workstation 100. In another embodiment, one or both of media 110, 120 may be included in a location remote from, but accessible to, workstation 100. For example, one or both of media 110, 120 may be included on a memory of a server networked to workstation 100 in a PACS system.

Workstation 100 can include a general purpose processing circuit, a network server interface, a software memory, and an image display monitor. For example, workstation 100 may be embodied in a personal computer networked in a PACS system.

Workstation 100 is also capable of or configured to retrieve and/or receive one or more sets of instructions from computer-readable storage medium 110. For example, a set of instructions may be communicated to workstation 100 from computer-readable storage medium 110 over a wired or wireless connection, for example. A set of instructions may be embodied in one or more computer software applications used to operate on one or more computer devices (such as workstation 100, for example) and cause such device(s) to carry out one or more steps directed by the set of instructions or some other set of instructions.

A set of instructions may include one or more software routines. These software routines include subsets of sets of instructions used to prescribe a course of action to be followed. In other words, a routine may include a software application within and/or used by a set of instructions or other software application. In general and unless otherwise stated herein, one or more routines described as included in a set of instructions may be embodied in one or more software applications that are included in a single software application or divided up among multiple software applications.

In operation, one or more images of a patient anatomy are obtained by one or more imaging modalities and stored as image data temporarily or permanently on computer-readable storage medium 120. Workstation 100 may retrieve or receive image data from medium 120 for display to one or more users. For example, a workstation 100 may retrieve or receive image data representative of a computed radiography ("CR") image of a patient's chest. A radiologist may then examine the image as displayed on a display device for any objects of interest such as, for example, tumors, lesions, etc.

As described above, an image may be marked as "significant." A user may desire to mark an image as significant for any number of reasons, as recognized by one of ordinary skill in the art. For example, an image may be marked as significant if one or more features or objects of interest appear in the image in a given location. A feature or an object of interest can include any item (such as an organ, a tumor, or lesion, for example) appearing in an image of a patient anatomy that is of interest to a user (for example, a radiologist). A feature or object of interest, or a grouping of features or objects of interest appearing in an image is an image pattern.

Figure 7:
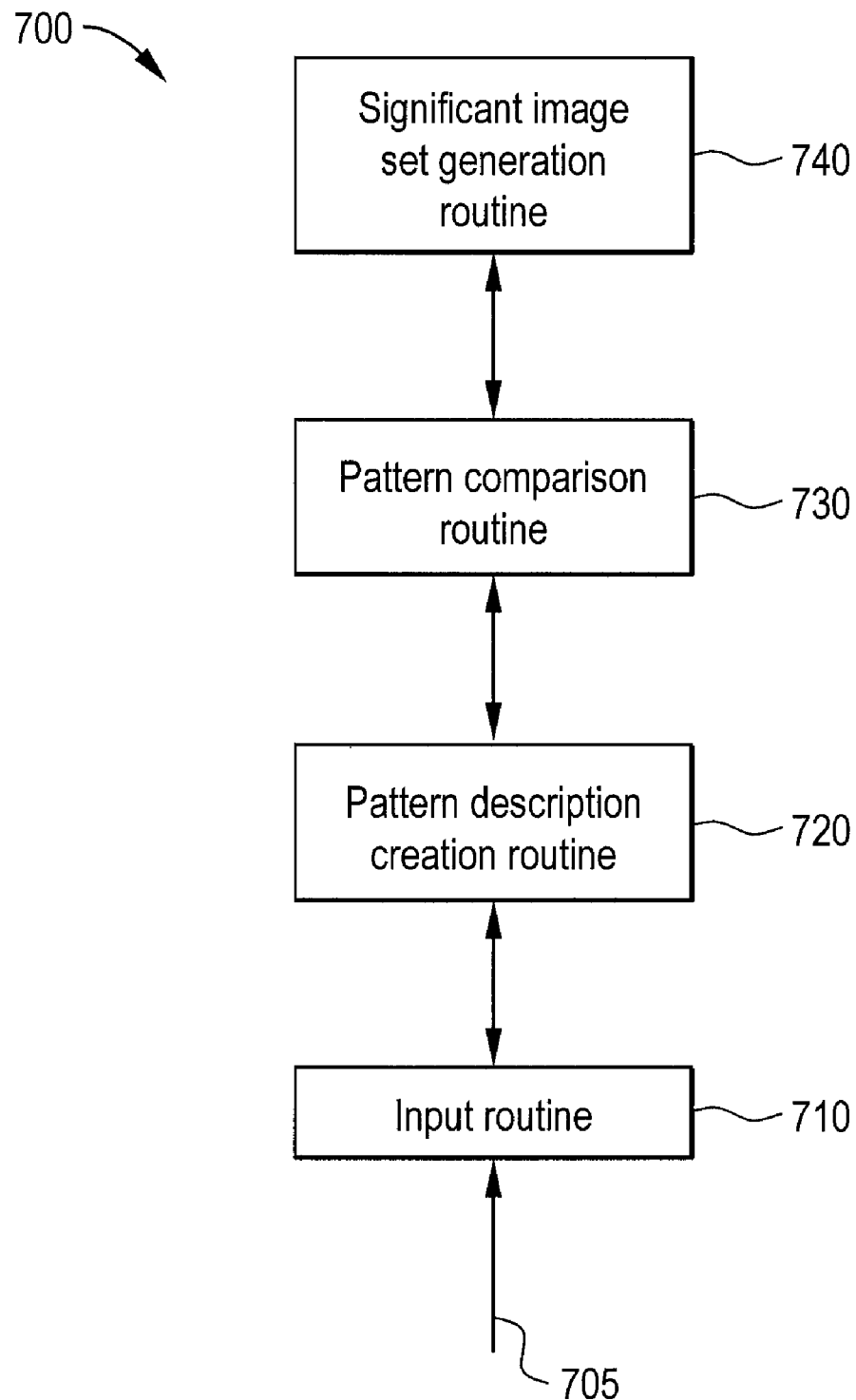
FIG. 7 illustrates a representation of such sets of instructions stored on a computer-readable storage medium in accordance with an embodiment of the present invention.

In an embodiment, one or more sets of instructions stored in a computer-readable storage medium (such as medium 110) are used by workstation 100 to receive input from a user, create a pattern description based on the user's input, compare a pattern description to one or more images, and/or generate a set of significant images automatically selected based on a comparison between a pattern description and one or more images. FIG. 7 illustrates a representation of such sets of instructions 700 stored on a computer-readable storage medium in accordance with an embodiment of the present invention. Sets of instructions 700 includes an input routine 710, a pattern description creation routine 720, a pattern comparison routine 730, and a significant image set generation routine 740.

Input routine 710 includes one or more sets of instructions stored on a computer-readable storage medium and can be embodied in a software application or portion of a software application configured to receive input from a user. This input can include information that identifies one or more patterns for a pattern description. A pattern description is a collection of one or more patterns in a representative significant image that are to be searched for in additional images, as described in more detail below.

A user may identify a pattern in a representative significant image by any way known to those of skill in the art. For example, a user may employ the input device to outline a shape of one or more patterns in the representative significant image.

In an embodiment of the present invention, a pattern may be automatically determined for a pattern description. For example, a pattern can be automatically generated by making use of image processing algorithms and filters. In an example, edge detection can be used to determine all edges available in an image. A filtering technique known to those of ordinary skill in the art may then be employed to filter all out one or more closed patterns in a representative significant image. These patterns can then be used to determine the pattern shapes in the image, which eventually can be made as a pattern.

Pattern description creation routine 720 includes one or more sets of instructions stored in a computer-readable storage medium (such as medium 110) and may be embodied in a software application or portion of a software application. Creation routine 720 may be used by workstation 100 to define or create a pattern description. The pattern description can be created from and based on input from a user. For example, a user can select an image as significant, thereby creating a representative significant image. The user may then create a pattern description based on the representative significant image. A user can create the pattern description by identifying one or more patterns in the representative significant image. For example, a user may employ an input device (such as a mouse, stylus, or keyboard, for example) connected to workstation 100 to identify one or more patterns. Input from the input device may be communicated to input routine 710 as pattern identification information 705.

The pattern description can include any data or information sufficient to describe the pattern(s) in the representative significant image. For example, the pattern description can include any one or more of a mathematical definition, a search boundary, and a pattern characteristic. The pattern description may be considered, by analogy, to be a template for describing one or more patterns in one or more representative significant images.

In an embodiment, the pattern description can include a mathematical definition of one or more shapes of the pattern(s) selected by the user in the representative significant image. The mathematical definition may include one or more mathematical equations that describe the shape of one or more patterns in the representative significant image.

The mathematical equations of the mathematical definition may be automatically determined by pattern description creation routine 720. For example, once a user identifies one or more patterns in a representative significant image, the user's input is used by pattern description creation routine 720 to determine the mathematical equation(s) that identify the shape of one or more patterns in the representative significant image. Pattern description creation routine 720 may determine the mathematical equation(s) by any manner known to those of ordinary skill in the art, including, for example, using regression methods to determine a best fit equation(s) for the selected pattern.

In an embodiment, pattern description creation routine 720 may also use information from the representative significant image to determine the mathematical equation(s) in the pattern description. For example, pattern description creation routine 720 may combine input from a user (such as the shape of an image area that the user has selected as including one or more patterns) in combination with image contrast levels. In other words, pattern description creation routine 720 may combine a user's input with one or more of a maximum gray scale level, a minimum gray scale level, a window gray scale level, and an average gray scale level to determine the mathematical equation(s) for the pattern description. For example, a user may select an image area in a representative significant image as defining a shape of a pattern. Pattern description creation routine 720 may then determine one or more mathematical equations to define the shape of the pattern by ensuring that all pixels near the image area selected by the user include a gray scale level that are less than a maximum level, that are greater than a minimum level, and/or that are within upper and lower gray scale levels (that is, a window gray scale level).

In another embodiment, a user may manually input the mathematical equations that define the shape of one or more patterns in a representative significant image.

In another embodiment, a user may modify the mathematical equation(s) determined by pattern description creation routine 720 as defining the shape of one or more patterns. For example, as described above, pattern description creation routine 720 may automatically determine the mathematical equation(s) for the shape(s) of one or more patterns selected by a user. Pattern description creation routine 720 may then communicate the equation(s) to workstation 100 so that a user may review the automatically determined equation(s). The user may then modify the equation(s) by modifying the equation(s) itself/themselves. For example, the user may modify the equation(s) in a manner similar to modifying text in a word processing application. However, while the word processing application analogy is provided, this example is provided merely as an example and not as a limitation on the present embodiment of the invention. Moreover, the equation(s) may be modified by any method known to those of ordinary skill in the art.

In another embodiment, the user may modify the equation(s) by using an input device to re-select the shape(s) of the pattern(s). For example, once a user sees the mathematical equation(s) determined by pattern description creation routine 720, the user may then modify the equation(s) by using an input device connected to workstation 100 to expand, reduce, and/or alter the shape of the pattern(s).

In an embodiment, the pattern description can include a search boundary. A search boundary can include any data or information sufficient to describe an image area. As described in more detail below, a search boundary can be used to limit the area in images that are searched for patterns or objects of interest that match a pattern description. For example, a search boundary can include one or more mathematical equations that define an image area. In general, a search boundary can be used to define an image area where one or more patterns are expected to be found in one or more images.

The mathematical equation(s) representing a search boundary may be automatically determined by pattern description creation routine 720. For example, once a user identifies one or more patterns in a representative significant image, the user's input is used by pattern description creation routine 720 to determine the mathematical equation(s) that identifies the image area selected by the user.

In an embodiment, the search boundary includes a standard shape or combination of standard shapes. A standard shape can include any common geometric shape such as a square, rectangle, circle, triangle, trapezoid, or parallelogram. A user may employ an input device connected to workstation 100 to select a center of the search boundary. Pattern description creation routine 720 may then define a search boundary as a standard shape (or combination of standard shapes) that is centered on the point selected by the user.

In an embodiment, the size of the standard shape(s) used as a search boundary is modifiable by a user. For example, a user may modify the size of the shape(s) by employing an input device connected to workstation 100 to click and drag on an edge of the search boundary and drag the edge to increase or decrease the size of the search boundary.

In another embodiment, the search boundary includes a shape defined by the user. The search boundary can include any shape, irregular or otherwise, that is defined by a user. For example, a user may employ an input device (such as a stylus or mouse) to manually outline the edges of a search boundary.

In an embodiment, the pattern description can include one or more pattern characteristics. A pattern characteristic can include any data or information sufficient to describe an imaging property of one or more patterns. For example, a pattern characteristic can include a minimum gray scale value or a maximum gray scale value of a pattern in an image. In another example, a pattern characteristic can include a distribution of pixel values. For example, a histogram of an image can include a graph that describes a distribution of pixel values. Such a histogram for an 8-bit gray scale image may span between 0 and 255 for the pixel values, for example. In general, a histogram differs for each image because of the pixel distribution. A shape of a histogram for a representative significant image may therefore be used as a pattern in a pattern description. In such an example, another image being examined may be determined to match the pattern description (as described in more detail below) if the distribution of pixel values in the image being examined matches the distribution of pixel values in a pattern description (within, for example, some amount of statistical threshold). The pattern characteristic may be identified by a user. For example, a user may employ a keyboard to type in the pattern characteristic.

In another example, a pattern characteristic can include a location of a pattern in an image. In another example, a pattern characteristic can include a relative distance of a pattern from an image boundary.

In another embodiment, the user may define a pattern description by selecting one or more pixels in the representative significant image. For example, a user may define a pattern characteristic by pointing a cursor or stylus to a pixel in a representative significant image that includes the pattern characteristic(s) desired by user.

In an embodiment, a pattern description can include one or more patterns in each of a plurality of representative significant images. A user may select two or more representative significant images on which to base a pattern description. For example, in a first representative significant image, a user may select one or more patterns to be included in a pattern description. The user may also select one or more patterns in another representative significant image to be included in the same pattern description. In this way, a pattern description can include a definition of multiple patterns appearing in multiple representative significant images.

Figure 9:
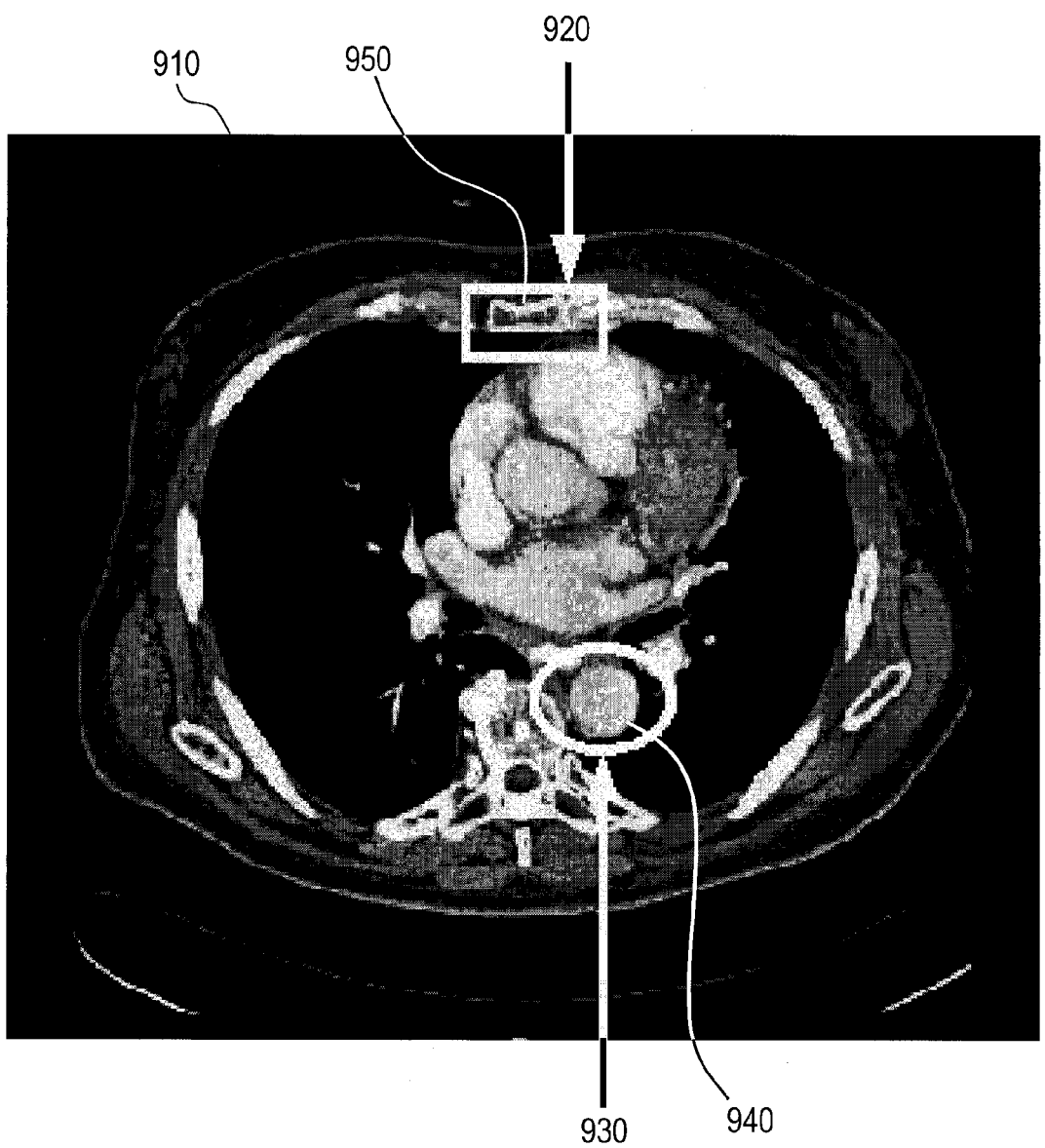
FIG. 9 illustrates an example representative significant image in accordance with an embodiment of the present invention.

FIG. 9 illustrates an example representative significant image 910 in accordance with an embodiment of the present invention. Image 910 includes a visual representation of a pattern description. The pattern description based on image 910 includes a first search boundary 920 and a second search boundary 930. As described herein, search boundaries 920, 930 may represent areas that are searched for patterns in additional images that are examined and compared to the pattern description. In addition, image 910 includes two patterns 940 and 950. Each one of these patterns 940, 950 may be characterized in a pattern description by a mathematical definition of its shape and/or by pattern characteristics, as described herein.

Once a pattern description has been created, the pattern description may be saved in any one or more of media 110, 120 and another computer-readable storage medium.

Pattern comparison routine 730 includes one or more sets of instructions stored in a computer-readable storage medium (such as medium 110) and may be embodied in a software application or portion of a software application. Comparison routine 730 may be used by workstation 100 to automatically calculate one or more amounts of match between a pattern description and one or more images. The pattern description can be compared to a plurality of images by comparison routine 730 to determine if one or more patterns in the images (herein referred to as "image patterns") match one or more of the patterns in the pattern description.

Pattern comparison routine 730 determines if one or more image patterns match at least one of the patterns in a pattern description. The pattern description may be created just before comparing it to one or more images or it may be saved and retrieved later for comparison to one or more images.

In an embodiment, pattern comparison routine 730 determines if one or more patterns appearing in images being examined match one or more patterns in a pattern description, where the images being examined and the representative significant image(s) upon which the pattern description is based are obtained from the same imaging modality.

In an embodiment, pattern comparison routine 730 determines if one or more patterns appearing in images being examined match one or more patterns in a pattern description, where the images being examined and the representative significant image(s) upon which the pattern description is based are obtained from two or more different imaging modalities.

In an embodiment, pattern comparison routine 730 determines if one or more patterns appearing in images being examined match one or more patterns in a pattern description, where the images being examined and the representative significant image(s) upon which the pattern description is based are from the same imaging study.

In an embodiment, pattern comparison routine 730 determines if one or more patterns appearing in images being examined match one or more patterns in a pattern description, where the images being examined and the representative significant image(s) upon which the pattern description is based are from two or more different imaging studies.

In an embodiment, pattern comparison routine 730 determines if one or more image patterns match at least one of the patterns in a pattern description by calculating an amount of match. The amount of match may be expressed in, for example, a percentage as a percentage match. However, any value denoting the amount of match between one or more patterns in a pattern description and an image may be used. For example, fractions or assigned values may be used to express an amount of match.

Pattern comparison routine 730 may compare a pattern description to all images included in an imaging study. When a pattern description is compared to an image, the image is considered as being examined. In an embodiment, the images being examined by pattern comparison routine 730 are included in the same imaging study as the representative significant image(s) that the pattern description is based on. In another embodiment, the images being examined by pattern comparison routine 730 are in an imaging study different from the imaging study(ies) that includes the representative significant image(s) that the pattern description is based on.

In an embodiment, a single amount of match is determined for each image being examined. For example, pattern comparison routine 730 may calculate a single percentage match between a pattern description and an image. Such a single amount of match may be derived from a comparison between a single pattern in the pattern description and the image. For example, pattern comparison routine 730 may determine an amount of match between each pattern in the pattern description and each image pattern. Pattern comparison routine 730 may then assign only one of these amounts of match to the image. For example, pattern comparison routine 730 may assign or correlate the maximum amount of match determined to the image.

In an embodiment, a plurality of amounts of matches is determined for each image being examined. For example, pattern comparison routine 730 may calculate a percentage match between each of a plurality of patterns in a pattern description and an image. Pattern comparison routine 730 may then assign each match amount to the image.

In another example, pattern comparison routine 730 may assign a single amount of match to an image by calculating an average amount of match between each pattern in the pattern description and the image being examined. While an average of matches is used as an example, any statistical analysis is within the scope of the invention described herein.

In an embodiment, a pattern description can include one or more shapes of one or more patterns, as described above. Pattern comparison routine 730 may then examine one or more images to determine if any one or more of the images includes one or more patterns that match the shape(s) in the pattern description. In other words, pattern comparison routine 730 can determine if any images have a pattern or object of interest have a similar shape as the shape(s) of the pattern description.

In an embodiment, pattern comparison routine 730 determines whether one or more patterns or objects of interest in an image match the mathematical equation(s) used to define one or more shapes in a pattern description. For example, comparison routine 730 may determine whether an image pattern is of a shape that fits within the mathematical equation(s) that define a pattern shape in a pattern description.

Pattern comparison routine 730 may determine whether an image pattern is of a given shape by determining one or more mathematical equations that define the image pattern shape. The(se) equation(s) may be determined by calculating the equation(s) that include all pixels of a given grayscale value in a given area, for example. In other words, pattern comparison routine 730 may determine that all pixels in an image pattern with a grayscale value that falls within a threshold window (that is, between lower and upper grayscale values) included in an image area form a shape defined by one or more equations.

In an embodiment, pattern comparison routine 730 can determine if one or more images have a pattern or object of interest with a similar shape by employing edge detection algorithms known to those of ordinary skill in the art. For example, edge detection algorithms can be employed to obtain all edges, including closed edges, of a possible matching pattern in an image being examined. This information can be used to determine the edges of the shape of the potentially matching pattern. In an example, pattern edges may be represented or described as a presence (represented by a binary 1, for example) or absence (represented by a binary 0, for example) of pixels, for example.

The closed edges can be matched to a known shape or a shape area, for example. Such a match may occur by comparing the number of pixels, area inside a pattern shape, and/or a distribution of pixels, for example. A percentage match (or any number demonstrating an amount of match) between a shape of a pattern in a pattern description and a shape of a potentially matching pattern in an image may then be calculated by determining how closely the pattern shape in the image being examined matches the pattern shape in the pattern description. For example, a percentage match may be determined by calculating how close the pattern shape in the pattern description matches a shape of a pattern found in the image being examined. A shape can be matched to a best fit circle (if searching for a pattern in the shape of a circle, for example) calculated by pattern comparison routine 730. Pattern comparison routine 730 may then use the calculated best fit circle (found to best match a pattern shape found in an examined image) and determine a fraction or percentage of overlap between the area of the best fit circle, for example, and the area of the pattern shape in the pattern description. This overlap may then be expressed as a percentage match. While a best fit circle is used in the above examples, any geometric shapes or combination of shapes may be used in accordance with embodiments of the present invention.

In an embodiment, pattern comparison routine 730 determines whether one or more image patterns are found within one or more search boundaries in a pattern description. As described above, a search boundary is an image area where one or more patterns are expected to be found in examined images. For example, a user may wish to define a search boundary of a desired size and/or shape (as described above) that includes an area in additional images to be searched for one or more patterns. The user may define such a search boundary in order to automatically select one or more additional significant images from a plurality of images when one or more patterns in the plurality of images appear in the search boundary, for example.

In an embodiment, pattern comparison routine 730 may determine an amount of match between a location of one or more patterns and a search boundary in a pattern description. The amount of match may be expressed in a percentage, for example. The percentage may be referred to as a percentage match, for example. The percentage match may include an amount of image area of a pattern or object of interest in an image that overlaps or is included in one or more search boundaries in the pattern description.

Figure 2:
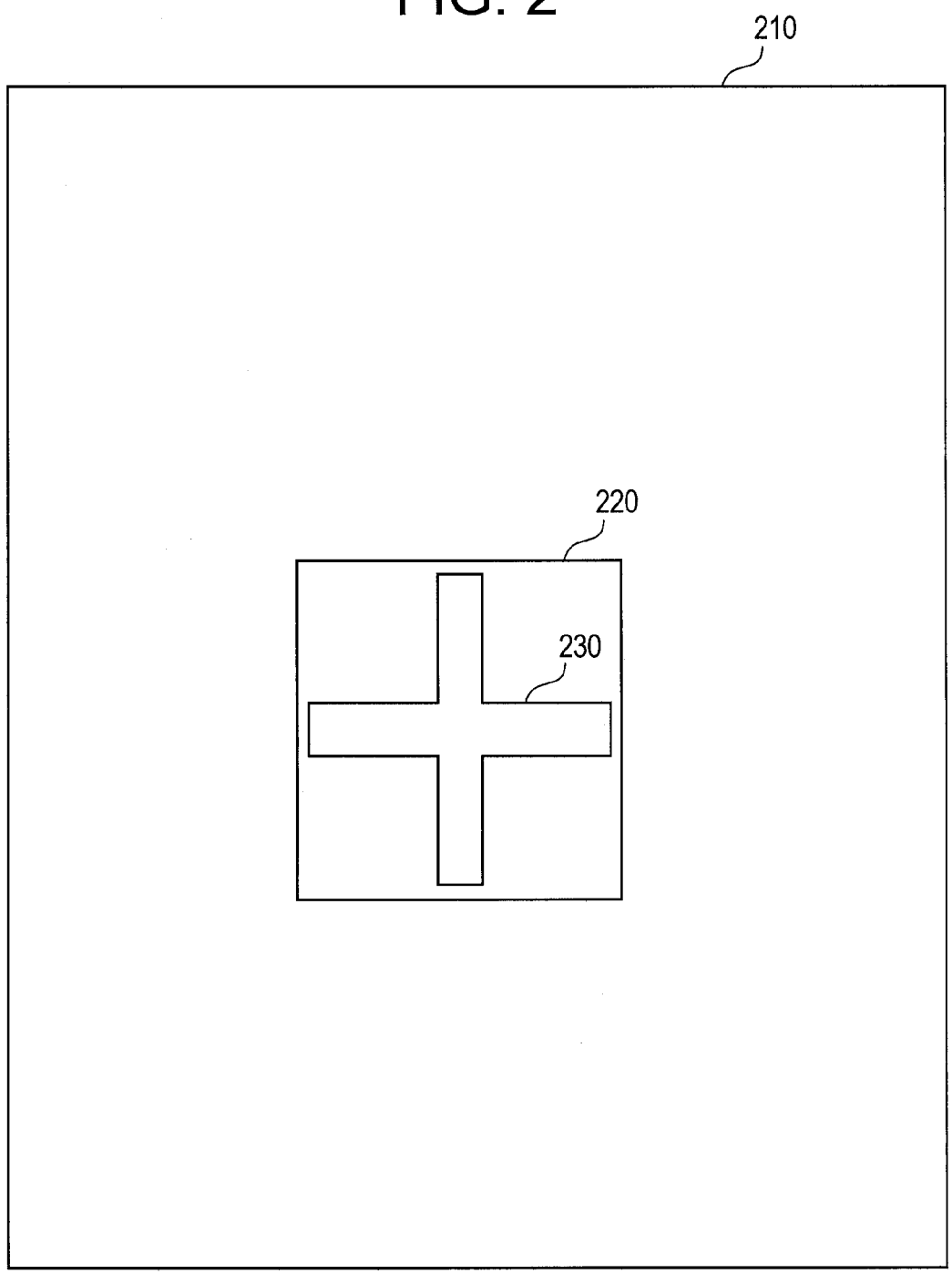
FIG. 2 illustrates a 100% match between an image pattern and a search boundary in an image in accordance with an embodiment of the present invention.

FIGS. 2-6 illustrate five examples of calculating a percentage match between an example image pattern 230 and an example search boundary 220 in an image 210 being examined in accordance with an embodiment of the present invention. FIG. 2 illustrates a 100% match between image pattern 230 and search boundary 220 in image 210 in accordance with an embodiment of the present invention. For example, in image 210 of FIG. 2, all of image pattern 230 is located within boundary 220. Therefore, upon comparison of a pattern description that includes search boundary 220 to image 210 that includes image pattern 230, a 100% match is determined or calculated. As described above, upon comparison of a pattern description to an image, one or more percentage matches may be calculated. Therefore, the 100% match between boundary 220 and image pattern 230 may be the only percentage match calculated upon comparing the pattern description to image 210. Alternatively, the 100% match may be one of a plurality of percentage matches that are calculated between the pattern description and image 210. Alternatively, the 100% match may be included in an average of a plurality of percentage matches that are calculated between the pattern description and image 210. Alternatively, the 100% match may be included in a weighted average of a plurality of percentage matches that are calculated between the pattern description and image 210.

Figure 3:
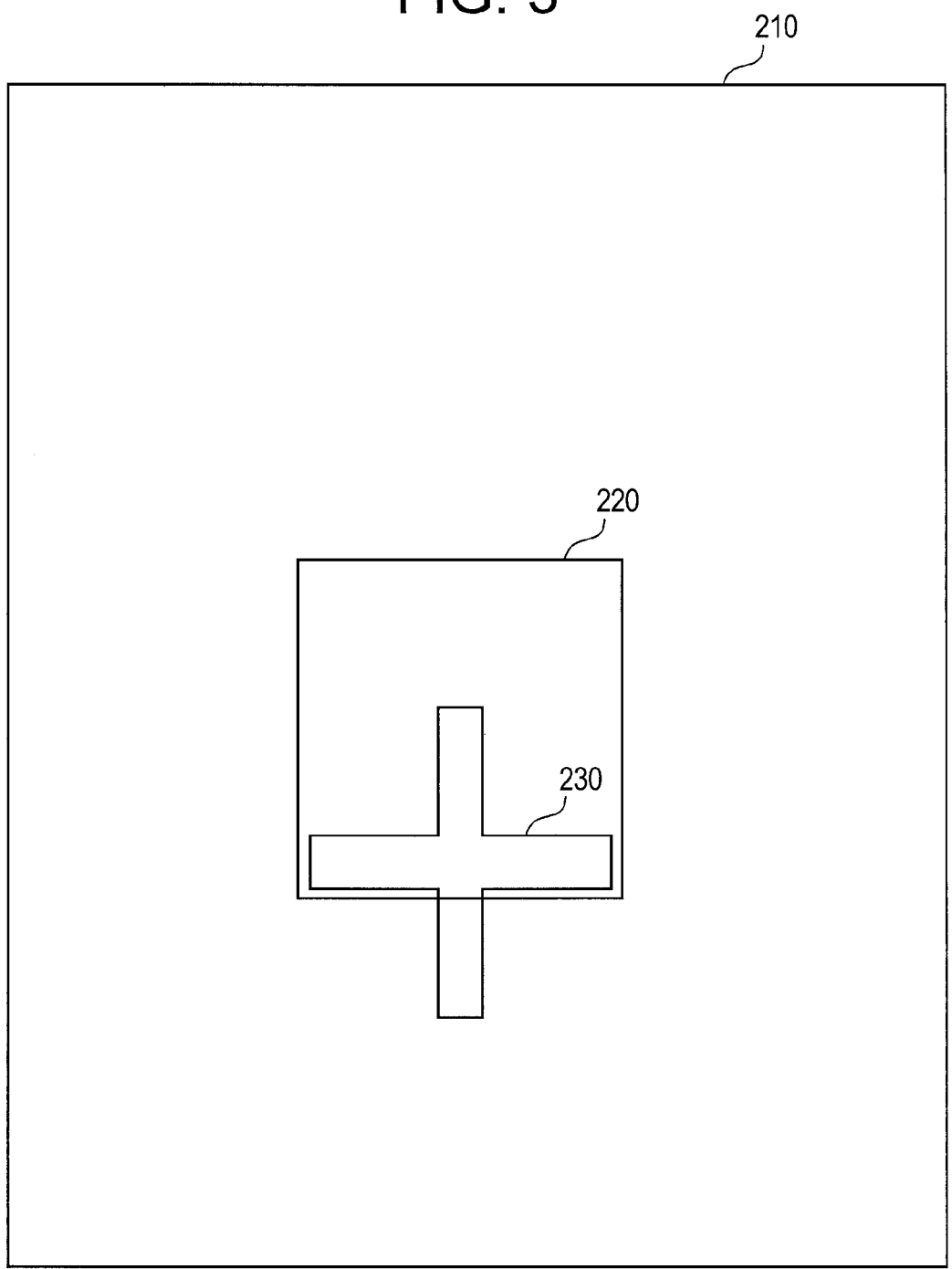
FIG. 3 illustrates an approximate 75% match between an image pattern and a search boundary in an image in accordance with an embodiment of the present invention.

FIG. 3 illustrates an approximate 75% match between image pattern 230 and search boundary 220 in image 210 in accordance with an embodiment of the present invention. For example, in image 210 of FIG. 3, approximately three-quarters of image pattern 230 is located within boundary 220. Therefore, upon comparison of a pattern description that includes search boundary 220 to image 210 that includes image pattern 230, a percentage match of approximately 75% is determined or calculated. As described above, the match of approximately 75% may be the only percentage match calculated, or it may be one of a plurality of percentage matches calculated.

Figure 4:
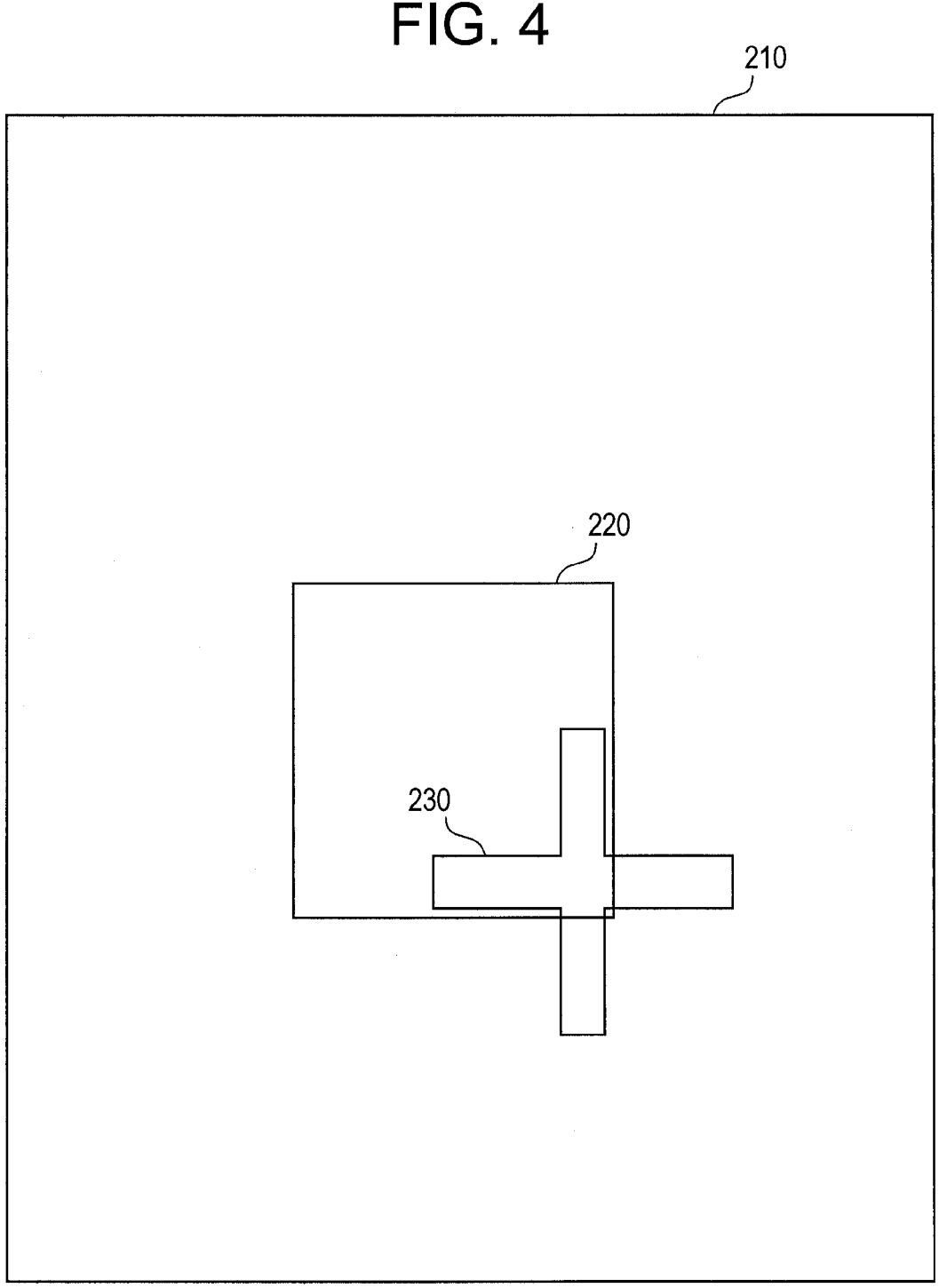
FIG. 4 illustrates an approximate 50% match between an image pattern and a search boundary in an image in accordance with an embodiment of the present invention.

FIG. 4 illustrates an approximate 50% match between image pattern 230 and search boundary 220 in image 210 in accordance with an embodiment of the present invention. For example, in image 210 of FIG. 4, approximately half of image pattern 230 is located within boundary 220. Therefore, upon comparison of a pattern description that includes search boundary 220 to image 210 that includes image pattern 230, a percentage match of approximately 50% is determined or calculated. As described above, this percentage match may be the only percentage match calculated, or it may be one of a plurality of percentage matches calculated.

Figure 5:
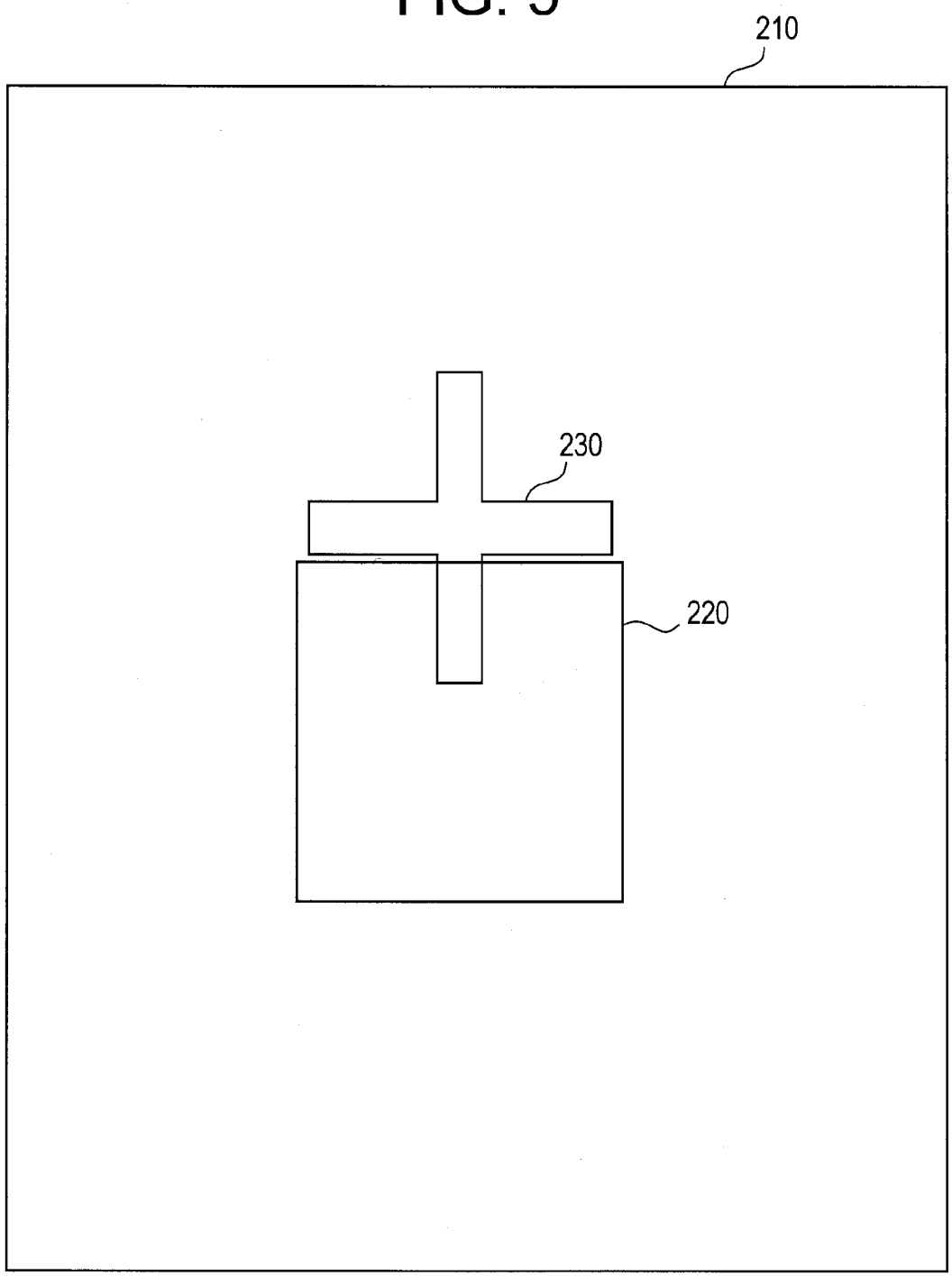
FIG. 5 illustrates an approximate 25% match between an image pattern and a search boundary in an image in accordance with an embodiment of the present invention.

FIG. 5 illustrates an approximate 25% match between image pattern 230 and search boundary 220 in image 210 in accordance with an embodiment of the present invention. For example, in image 210 of FIG. 5, approximately one-quarter of image pattern 230 is located within boundary 220. Therefore, upon comparison of a pattern description that includes search boundary 220 to image 210 that includes image pattern 230, a percentage match of approximately 25% is determined or calculated. As described above, this percentage match may be the only percentage match calculated, or it may be one of a plurality of percentage matches calculated.

Figure 6:
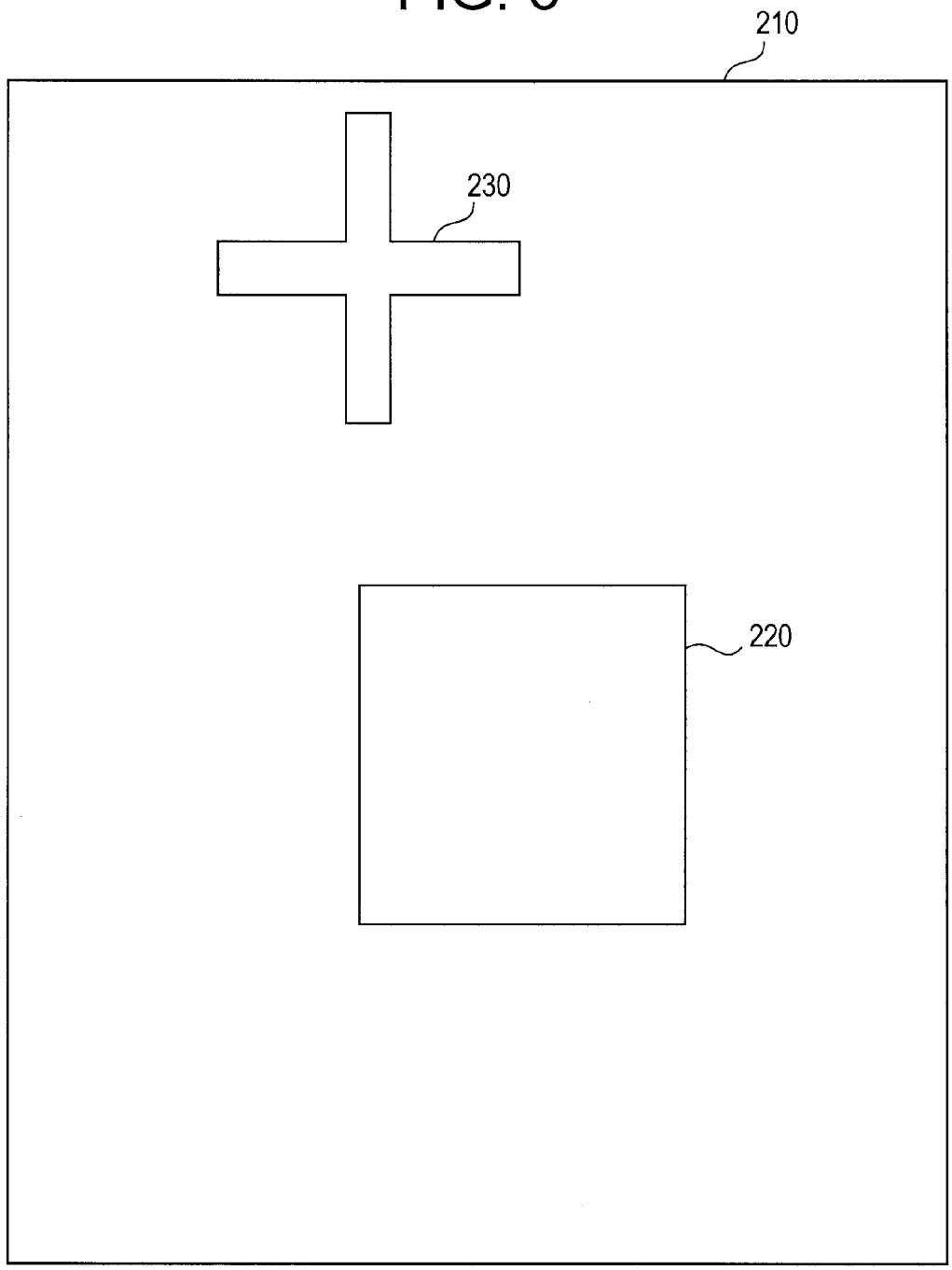
FIG. 6 illustrates an approximate 0% match between an image pattern and a search boundary in an image in accordance with an embodiment of the present invention.

FIG. 6 illustrates an approximate 0% match between image pattern 230 and search boundary 220 in image 210 in accordance with an embodiment of the present invention. For example, in image 210 of FIG. 6, none of image pattern 230 is located within boundary 220. Therefore, upon comparison of a pattern description that includes search boundary 220 to image 210 that includes image pattern 230, a percentage match of approximately 0% is determined or calculated. As described above, this percentage match may be the only percentage match calculated, or it may be one of a plurality of percentage matches calculated.

In an embodiment, pattern comparison routine 730 may determine an amount of match between one or more pattern characteristics in a pattern description and one or more characteristics of one or more image patterns. The amount of match may be expressed in a percentage, for example.

In an embodiment, the percentage match for a pattern description can be calculated by determining an amount of similarity or match between pixel distributions in the image being examined and the pattern description. For example, a histogram representative of the pixel distribution in an image being examined and a histogram representative of the pixel distribution in a pattern description may be compared to determined a percentage match.

In an embodiment, the percentage match for a pattern description can be calculated by comparing pixel value distributions in a pattern description and in an image being examined. For example, a histogram representative of the pixel value distribution in an image being examined and a histogram representative of the pixel value distribution in a pattern description may be compared to determined a percentage match between the two distributions. However, while a histogram is used as an example of a representation of a pixel distribution, another statistical representation of pixel distribution may also be used. For example, a normal curve (also known as the "bell curve"), a Student's t distribution, a chi-square distribution, and/or an F distribution may be used.

In an embodiment of the present invention, a pattern description can include a plurality of patterns from a plurality of representative images. For example, a pattern description can include a first mathematical definition of a first shape in a first representative image, a second mathematical definition of a second shape in a second image, first and second search boundaries, and a first pattern characteristic from a third representative image. Therefore, the pattern description comprises two shapes from two representative images, two search boundaries, and a third pattern characteristic from a third representative image. Pattern comparison routine 730 may then determine one or more amounts of match based on the pattern description, as described above, with the only difference being that the pattern description was obtained from more than one representative significant image.

Significant image set generation routine 740 includes one or more sets of instructions stored in a computer-readable storage medium (such as medium 110) and may be embodied in a software application or portion of a software application. Generation routine 740 may be used by workstation 100 to automatically select one or more additional significant images from a plurality of images for inclusion in a set of significant images. The selection of an image for inclusion in a set of significant images may be based on the calculation of one or more amounts of match between a pattern description and the image, as described above.

Once pattern comparison routine 730 has determined one or more amounts of match between a pattern description and one or more images, significant image set generation routine 740 compares the amount(s) of match to one or more thresholds. For example, if comparison routine 730 assigns a single percentage match to a given image (whether by determining only a single percentage match or by averaging all percentage matches, as described above, for example), generation routine 740 may compare the percentage match to a single threshold. If the percentage match is greater than or exceeds the threshold, generation routine 740 automatically includes the image in a set of significant images. By doing so, generation routine 740 has automatically marked the image as significant.

In an embodiment, if comparison routine 730 has determined a plurality of amounts of match between a pattern description and an image, generation routine 740 may compare each amount of match to a single threshold. If any one of the amounts of match is greater than or exceeds the threshold, generation routine 740 automatically includes the image in a set of significant images.

In an embodiment, if comparison routine 730 has determined a plurality of amounts of match between a pattern description and an image, generation routine 740 may compare each amount of match to a single threshold. If a user-configurable number of the amounts of match is greater than or exceeds the threshold, generation routine 740 automatically includes the image in a set of significant images.

In an embodiment, if comparison routine 730 assigns a single percentage match to a given image (whether by determining only a single percentage match or by averaging all percentage matches, as described above, for example), generation routine 740 may compare the percentage match to one or more of a plurality of thresholds. The plurality of thresholds may define one or more subsets of significant images. For example, a plurality of thresholds may include: 100%, 95%, 90%, 80% and 70%. These thresholds may then define a five subsets of significant images as:

(1) X=100%;
(2) 100%>X≧95%;
(3) 95%>X≧90%;
(4) 90%>X≧80%; and
(5) 80%>X≧70%.

If the percentage match for an image exceeds a threshold for a given subset of significant images, generation routine 740 automatically includes the image in the subset, but not in any other subset. By doing so, generation routine 740 has automatically marked the image as significant. For example, given the following images with their percentage match shown in a corresponding column in the following table, each image is included in a subset of significant images as described above:

| Image | Percentage Match | Subset # |
|-------|------------------|----------|
| A | 67% | None |
| B | 88% | 4 |
| C | 99% | 2 |
| D | 100% | 1 |
| E | 95% | 2 |
| F | 92% | 3 |
| G | 79% | 5 |

In another embodiment, if comparison routine 730 assigns a single percentage match to a given image (whether by determining only a single percentage match or by averaging all percentage matches, as described above, for example), generation routine 740 may compare the percentage match to one or more of a plurality of thresholds. The plurality of thresholds may define one or more subsets of significant images. For example, a plurality of thresholds may include: 100%, 95%, 90%, 80% and 70%. These thresholds may then define a five subsets of significant images as:

(1) X=100%;
(2) X≧95%;
(3) X≧90%;
(4) X≧80%; and
(5) X≧70%.

If the percentage match for an image exceeds a threshold for a given subset of significant images, generation routine 740 automatically includes the image in the subset, as well as any other subset to which the image belongs. In other words, a given image with a given percentage match may be included in multiple subsets. By doing so, generation routine 740 has automatically marked the image as significant. For example, given the following images with their percentage match shown in a corresponding column in the following table, each image is included in a subset of significant images as described above:

| Image | Percentage Match | Subset #s |
|-------|------------------|-----------|
| A | 67% | None |
| B | 88% | 4, 5 |
| C | 99% | 2, 3, 4, 5 |
| D | 100% | 1, 2, 3, 4, 5 |
| E | 95% | 2, 3, 4, 5 |
| F | 92% | 3, 4, 5 |
| G | 79% | 5 |

In an embodiment, when comparison routine 730 determines a plurality of amounts of match for a given image, generation routine 740 may determine whether to mark the image as significant and/or which set or subset of significant images to include the image in based on the greatest amount of match. In another embodiment, generation routine 740 may determine whether to mark the image as significant and/or which set or subset of significant images to include the image in based on the smallest amount of match. In another embodiment, generation routine 740 may determine whether to mark the image as significant and/or which set or subset of significant images to include the image in based on an average or other statistical analysis of the amounts of match.

In an embodiment, when generation routine 740 has determined that an image is significant, generation routine 740 changes an attribute associated with the image in the image header to reflect the image's status as significant.

In another embodiment, when generation routine 740 has determined that an image is significant, generation routine 740 changes an attribute associated with the image in a database to reflect the image's status as significant. This database may be located in either first or second computer-readable storage media 110, 120 and/or on workstation 100. In an embodiment, the database may be located in a computer-readable storage media remote to workstation 100.

In another embodiment, when generation routine 740 has determined that an image is significant, generation routine 740 attaches the image to a series of significant images. In this way, generation routine 740 creates a growing series of significant images.

In an embodiment, when generation routine 740 has determined that an image is significant, generation routine 740 causes the image to be copied from its current memory location in a computer-readable storage medium (such as media 110 or 120) to a different location in the same or different media where a set of significant images is stored. In other words, an image automatically selected as significant is automatically copied to a location with other automatically selected significant images. In an embodiment, this location is the same location as the representative significant image(s) upon which the pattern description is based. For example, the automatically marked significant images may be included in the same imaging study as the representative significant image(s) upon which the pattern description was based. In another embodiment, this location is different from the location where the representative significant image(s) upon which the pattern description is based are stored. For example, the automatically marked significant images may be included in a different imaging study that the representative significant image(s) upon which the pattern description was based are stored.

In an embodiment, when generation routine 740 has determined that an image is significant, generation routine 740 causes the image to be moved from its current memory location in a computer-readable storage medium (such as media 10 or 120) to a different location in the same or different media where a set of significant images is stored. In other words, an image automatically selected as significant is automatically moved to a location with other automatically selected significant images. In an embodiment, this location is the same location as the representative significant image(s) upon which the pattern description is based. For example, the automatically marked significant images may be included in the same imaging study as the representative significant image(s) upon which the pattern description was based. In another embodiment, this location is different from the location where the representative significant image(s) upon which the pattern description is based are stored. For example, the automatically marked significant images may be included in a different imaging study that the representative significant image(s) upon which the pattern description was based are stored.

Figure 8:
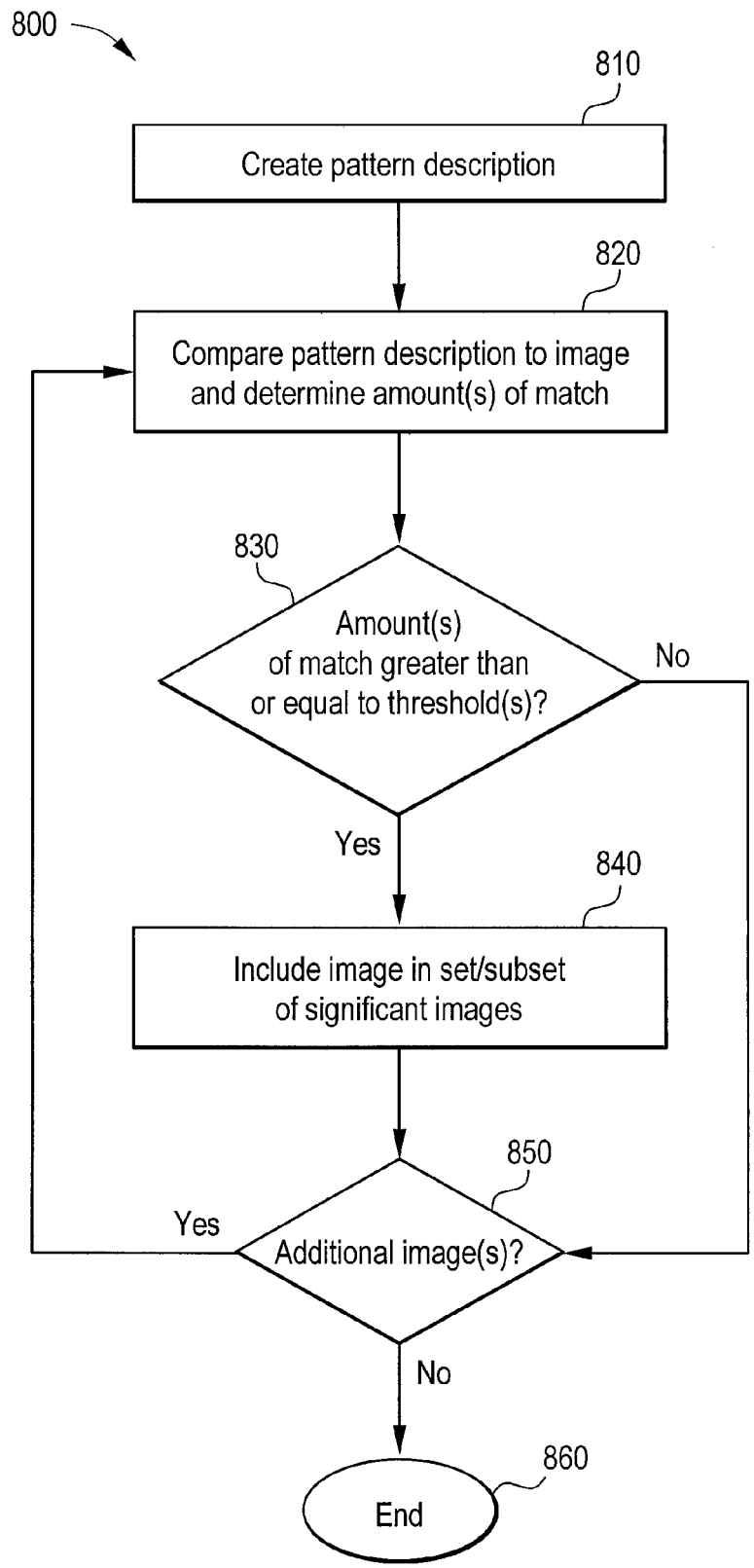
FIG. 8 illustrates a flowchart of a method for automatically selecting one or more images as significant in accordance with an embodiment of the present invention.

FIG. 8 illustrates a flowchart of a method 800 for automatically selecting one or more images as significant in accordance with an embodiment of the present invention. First, at step 810, a pattern description is created based on one or more representative significant images, as described above. Next, at step 820, the pattern description is compared to an image, as described above. The image may be included in the same imaging study as the representative significant image(s) or in a different imaging study. In addition, the image may be one of a plurality of images to be compared to the pattern description. As the pattern description is compared to the image, one or more amounts of match are determined, as described above.

Next, at step 830, a determination of whether one or more of the amounts of match determined at step 820 are greater than or equal to one or more thresholds, as described above. In an embodiment, if one of the amounts of match determined at step 820 is greater than or equal to one or more thresholds, method 800 proceeds to step 840. If none of the amounts of match determined at step 820 are greater than or equal to one or more thresholds, method 800 proceeds to step 850.

In another embodiment, at step 830, a determination of whether an average or other statistical analysis of one or more of the amounts of match determined at step 820 are greater than or equal to one or more thresholds, as described above. In an embodiment, if the average or statistical analysis is greater than or equal to one or more thresholds, method 800 proceeds to step 840. If average or statistical analysis is not greater than or equal to one or more thresholds, method 800 proceeds to step 850.

In another embodiment, at step 830, a determination of whether one or more amounts of match determined at step 820 falls within a window of thresholds. As described above, a plurality of thresholds may be used to define upper and lower boundaries of a subset of significant images. At step 830, one or more amounts of match are compared to the various thresholds that define the subsets of significant images. If any of the amounts of match fall within one of the upper and lower boundaries of a subset, method 800 proceeds to step 840. Otherwise, method 800 proceeds to step 850.

In another embodiment, at step 830, a determination of whether one or more amounts of match determined at step 820 exceeds one or more thresholds, where each threshold defines a lower limit of a subset of significant images. As described above, a plurality of thresholds may be used to define lower boundaries of a subset of significant images. At step 830, one or more amounts of match are compared to the various thresholds that define the lower boundaries of the subsets of significant images. If any of the amounts of match exceed one or more lower boundaries of one or more subsets, method 800 proceeds to step 840. Otherwise, method 800 proceeds to step 850.

At step 840, the image is included in a set or subset of significant images, as described above. Next, at step 850, a determination of whether one or more additional images are to be examined is performed. If it is determined that one or more additional images are to be examined, method 800 proceeds to step 820. In other words, method 800 proceeds in a loop-wise fashion through steps 820, 830, 840 and 850 until all images desired to be examined are compared to the pattern description. If it is determined that no additional images are to be examined, method 800 proceeds to step 860. At step 860, method 800 terminates. Therefore, once all images desired to be examined are compared to the pattern description and they are either selected to be automatically marked as significant or not so selected, method 800 terminates.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A method for automatic significant image generation based on image characteristics, said method including:
   comparing a pattern description to one or more images, said pattern description including one or more patterns based on a representative image;
   based on said comparing step, selecting at least one significant image from said one or more images; and
   creating said pattern description by identifying one or more patterns in said representative image, wherein said pattern description includes at least one of:
   a mathematical definition of one or more shapes of each of said patterns in said representative image;
   a search boundary of one or more of said patterns in said representative image; and
   one or more pattern characteristics of said patterns in said representative image.

2. The method of claim 1, wherein said comparing step includes determining if a pattern in one or more of said images matches at least one of said patterns in said pattern description.

3. The method of claim 2, wherein said comparing step further includes calculating a percentage match between said pattern description and each of said of images.

4. The method of claim 3, wherein said selecting step includes selecting said at least one significant image if said percentage match exceeds a threshold percentage.

5. The method of claim 1, further including adding said at least one significant image to a set of selected significant images.

6. The method of claim 1, wherein said pattern characteristics include one or more of a minimum gray scale value, a maximum gray scale value, a distribution of pixel values, a location of a pattern, and a distance of a pattern from an image boundary.

7. The method of claim 1, wherein said search boundary includes an image area where one or more of said patterns in said representative image is expected to be found in a corresponding image area of one or more of said images.

8. The method of claim 1, wherein said comparing step includes determining one or more of:
    if a shape of a pattern in one or more of said images matches said mathematical definition of said pattern description;
    if a pattern in one or more of said images is located within said search boundary; and
    if a characteristic of a pattern in one or more of said images matches one or more of said pattern characteristics of said pattern description.

9. The method of claim 1, wherein said patterns represent one or more objects of interest in said representative image.

10. The method of claim 1, wherein said representative image and said images are included in a single comparison imaging study.

11. The method of claim 1, wherein said representative image and said images are included in different comparison imaging studies.

12. The method of claim 1, further including creating said pattern description by identifying one or more patterns in each a plurality of representative images.

13. The method of claim 12, wherein said comparing step includes calculating a plurality of percentage matches between each of said patterns in said pattern description and one or more of said images.

14. The method of claim 13, wherein said selecting step includes selecting said at least one significant image if any of said percentage matches exceed a threshold percentage.

15. A computer-readable storage medium including a set of instructions for a computer, said instructions including:
    a pattern comparison routine configured to compare a pattern description to one or more images, said pattern description including one or more patterns in a representative image; and
    a significant image set generation routine configured to select at least one significant image from said images, wherein said comparison routine is configured to determine if a pattern in one or more of said images matches at least one of said patterns in said pattern description, said comparison routine is configured to calculate a percentage match between said pattern description and each of said images, and said significant image set generation routine is configured to select said at least one significant image if said percentage match exceeds a threshold percentage.

16. The set of instructions of claim 15, wherein said significant image set generation routine is configured to select said at least one significant image based on one or more comparisons performed by said comparison routine.

17. The set of instructions of claim 15, further including a pattern description creation routine configured to create said pattern description based on an identification of one or more patterns in said representative image.

18. The set of instructions of claim 17, wherein said pattern description includes at least one of:
    a mathematical definition of one or more shapes of each of said patterns in said representative image;
    a search boundary of one or more of said patterns in said representative image; and
    one or more pattern characteristics of said patterns in said representative image.

19. The set of instructions of claim 18, wherein said pattern characteristics include one or more of a minimum gray scale value, a maximum gray scale value, a distribution of pixel values, a location of a pattern, and a distance of a pattern from an image boundary.

20. The set of instructions of claim 18, wherein said search boundary includes an image area where one or more of said patterns in said representative image is expected to be found in a corresponding image area of one or more of said images.

21. The set of instructions of claim 18, wherein said pattern comparison routine is configured to determine one or more of:
    if a shape of a pattern in one or more of said images matches said mathematical definition of said pattern description;
    if a pattern in one or more of said images is located within said search boundary; and
    if a characteristic of a pattern in one or more of said images matches one or more of said pattern characteristics of said pattern description.

22. The set of instructions of claim 17, wherein said patterns represent one or more objects of interest in said representative image.

23. The set of instructions of claim 15, wherein said significant image set generation routine is configured to add said at least one significant image to a set of selected significant images.

24. The set of instructions of claim 15, wherein said representative image and said plurality of images are included in a single comparison imaging study.

25. The set of instructions of claim 15, wherein said representative image and said plurality of images are included in different comparison imaging studies.

26. The set of instructions of claim 15, further including a pattern description creation routine configured to create said pattern description based on an identification of one or more patterns in each a plurality of representative images.

27. The set of instructions of claim 26, wherein said pattern comparison routine is configured to calculate a plurality of percentage matches between each of said patterns in said pattern description and one or more of said images.

28. The set of instructions of claim 27, wherein said significant image set generation routine is configured to select said at least one significant image if any of said percentage matches exceed a threshold percentage.

* * * * *

UNITED STATES PATENT AND TRADEMARK OFFICE
CERTIFICATE OF CORRECTION

PATENT NO. : 7,639,890 B2 Page 1 of 1
APPLICATION NO. : 11/257871
DATED : December 29, 2009
INVENTOR(S) : Kuriathungal et al.

It is certified that error appears in the above-identified patent and that said Letters Patent is hereby corrected as shown below:

In col. 15, line 14, delete "10" and insert --110--.

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO.       : 7,639,890 B2                                                                Page 1 of 1
APPLICATION NO.  : 11/257871
DATED            : December 29, 2009
INVENTOR(S)      : Kuriathungal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1100 days.

Signed and Sealed this

Ninth Day of November, 2010

David J. Kappos
*Director of the United States Patent and Trademark Office*